US005259372A

United States Patent [19]

Gross et al.

[11] Patent Number: 5,259,372

[45] Date of Patent: Nov. 9, 1993

[54] OXYGEN CYLINDER CARRIER APPARATUS PARTICULARLY FOR STRETCHERS

[76] Inventors: Betty J. Gross, 13631 E. Morgan, Gilbert, Ariz. 85234; James A. Maloney, 17824 N. 57th Dr., Glendale, Ariz. 85308

[21] Appl. No.: 721,092

[22] Filed: Jun. 24, 1991

[51] Int. Cl.$^5$ .......... A61M 15/00

[52] U.S. Cl. .......... 128/200.24; 128/204.18

[58] Field of Search .......... 128/200.24, 202.18, 128/203.13, 205.22, 204.18; 296/20; 5/503.1, 625; 248/214

[56] References Cited

U.S. PATENT DOCUMENTS

| | | | |
|---|---|---|---|
| 2,406,888 | 9/1946 | Meidenbauer | 128/205.22 |
| 3,304,116 | 2/1967 | Stryker | 296/20 |
| 3,761,968 | 10/1973 | Besler | 5/503.1 |
| 4,352,991 | 10/1982 | Kaufman | 296/20 |
| 4,383,528 | 5/1983 | Eppolito | 128/205.22 |
| 4,438,764 | 3/1984 | Eppolito | 128/205.22 |
| 4,606,521 | 8/1986 | Williams | 248/214 |
| 4,646,860 | 3/1987 | Owens et al. | 296/20 |
| 4,685,456 | 8/1987 | Smart | 128/205.22 |
| 4,739,913 | 4/1988 | Moore | 128/205.22 |
| 4,979,659 | 12/1990 | Boyd | 128/205.22 |
| 4,996,982 | 3/1991 | Williamson | 128/205.22 |
| 5,179,746 | 1/1993 | Rogers | 5/625 |

FOREIGN PATENT DOCUMENTS

| | | | |
|---|---|---|---|
| 2285113 | 4/1976 | France | 296/20 |

*Primary Examiner*—Edgar S. Burr
*Assistant Examiner*—Aaron J. Louis
*Attorney, Agent, or Firm*—H. Gordon Shields

[57] ABSTRACT

An oxygen bottle carrier apparatus is particularly designed for securing a "D" size oxygen storage cylinder to a medical patient transport stretcher for transport to, from, or in an emergency medical transport vehicle. The carrier apparatus includes a flexible, coated material bag, open at one end, with a drawstring closure and adjustable straps adapted to be mounted on the upper framework of the stretcher in unused space just in front of the upper and lower frame members of the stretcher at its head end. The adjustability of the straps allows for use of the apparatus with various models of stretchers. The oxygen bottle is inserted through the open end of the bag so that only the bottle stem and associated valves and gauges protrudes from the bag. The bag is then closed using the drawstring closure. The apparatus is then mounted to the head end of the stretcher upper frame members by use of two straps located at either end of the bag. The straps, when connected using attached buckles and "Velcro" type fasteners, form a closed loop around both the oxygen bottle bag and the frame of the stretcher, and allow the oxygen bottle to be suspended in the potential space that exists between the upper and lower framework of the head end of the stretcher.

8 Claims, 2 Drawing Sheets

OXYGEN CYLINDER CARRIER APPARATUS PARTICULARLY FOR STRETCHERS

FIELD OF THE INVENTION

This invention relates to an oxygen cylinder carrier attachment for a conveyance, and particularly to an oxygen cylinder carrier attachment for a medical patient transport stretcher.

BACKGROUND OF THE INVENTION

It is quite often necessary for oxygen (O2) to be administered to a patient while he is being conveyed on an ambulance stretcher, during the time that he is being carried on the stretcher to the ambulance, while the ambulance is traveling to the hospital or other medical facility, and while the patient is being removed from the ambulance at the hospital or other emergency facility. To our knowledge, both in the past and at present, it is generally the practice to either place the oxygen cylinder on the stretcher with the patient, or to mount the cylinder on the side of the stretcher using a metal bracket type of device. A third option that is used is to have an additional person carry the cylinder, while the patient is being moved on the stretcher.

Particularly during the time while the stretcher is being removed from, or is entering into, a building, none of these methods is satisfactory. For instance, an extra person may not always be available to assist in holding the cylinder. Even when available, this makes for a difficult procedure, since residential doorways, hallways, stairways, or the placement of furniture in the residence usually is not designed for the simultaneous passage of a stretcher and another person.

The same problems cited above are usually encountered using stretchers that have a side-mounted carrying device. Doorways, stairwells, and hallways are not usually wide enough to accommodate the stretcher with the side carrier attached, and as a result, walls, furniture, of valuable oxygen equipment can and sometimes is damaged. Besides, the additional weight concentrated on one side of the stretcher throws the stretcher off balance when it is lifted, causing an additional burden to the stretcher bearers and a possible unsafe situation for the patient.

It is also not very satisfactory to place the oxygen cylinder on the stretcher with the patient. Despite all of its advantages, an oxygen cylinder is not a desirable bedfellow for an emergency patient. Also, when the cylinder is placed on the stretcher with the patient, the stretcher bearers are often forced to do a juggling act to keep the patient or the oxygen cylinder from falling off the stretcher when it is being lifted. Even if the cylinder does remain on the stretcher, it may protrude from it, striking door-jambs, furniture, and the like, again causing unnecessary damage.

It has been previously proposed to provide special cylinder carriers for such stretchers, two examples being U.S. Pat. Nos. 3,427,668 and 3,761,968, which disclose cylinder carriers mounted over the feet of the patient and beneath the head end of the stretcher, respectively. To our knowledge, however, neither of these proposals have been adopted to any substantial extent, if at all.

SUMMARY OF THE INVENTION

In general, it is the object of the present invention to provide a cylinder carrier for attachment to a conveyance, particularly an oxygen cylinder carrier for attachment to an ambulance stretcher. This carrier is characterized by its advantageous location, its ease in mounting, its adaptability to fit different models and sizes of stretchers, and the ease in which the oxygen cylinder can be removed or inserted. The present carrier attachment apparatus is mounted on the stretcher in an out-of-the-way location, but it is still readily accessible, and the gauges are readily visible. The apparatus locates the oxygen cylinder where it is needed, close to the patient's head. The apparatus utilizes unused space that lies within the lateral bounds of the sides of the stretcher, and which space would otherwise be wasted. The present invention does not contribute to the top-heaviness of the stretcher. The apparatus is easily mounted on the stretcher and is adjustable for different sizes of models of stretchers. The apparatus of the present invention facilitates quick removal or replacement of an empty oxygen cylinder while securely holding the oxygen cylinder near the action, by the patient's head.

Toward achieving the above noted advantageous characteristics, we have provided a cylinder holder that mounts to the bottom portion of the "U" shaped, horizontal, patient torso supporting frame that is on each medical stretcher. This portion of the stretcher allows the patients torso to be elevated to various planes from horizontal to near vertical. The cylinder carrier is oriented so that its length it within the plane of the width of the stretcher with the mouth and, consequently, the regulator/stem portion of the oxygen cylinder orientated towards the left side of the stretcher (as an observer would be looking at the stretcher facing the head end). Our carrier apparatus utilizes adjustable straps which loop around the tubular framework of the patient's upper torso supporting frame of the stretcher and then attaches to a flexible, coated material bag that encloses the oxygen cylinder, continuing around both the bag and the cylinder to form a closed loop. This allows the oxygen cylinder to be suspended slightly below and in front of the "U" shaped torso supporting structure.

A second adjustable strap is looped through the framework beneath the mattress of the stretcher and is attached to both the top and bottom ends of the carrier. When tension is applied by tightening this strap, the oxygen cylinder is rotated up to a position near level with the patient stretcher mattress, and slightly in front of the stretcher.

The flexible bag is sewn closed at the bottom end of the bag and is closed at the top end, or mouth, of the bag using a drawstring closure. Once the bottle is inserted into the bag, only the valve stem/regulator assembly protrudes from the bag mouth. Once the drawstring closure is tightened, lateral movement of the oxygen cylinder is prevented. Once installed on the ambulance stretcher the carrier, itself, need not be removed from the stretcher.

If removal of the oxygen cylinder is desired from replacement or refilling, the drawstring is loosened, which allows the mouth of the bag to open, and the cylinder is withdrawn, refilled, and/or replaced. Included in the present apparatus is a handle that runs the length of the flexible bag that allows for hand carrying of the oxygen cylinder carrier, in the unlikely event such is required. Also included in the design is a small pocket attached to the side of the carrier for holding an oxygen cylinder "key" or a small wrench for turning on and off the oxygen cylinder. In addition to its functional advantages, the present invention also lends itself to economical manufacture, and is of simple but sturdy and reliable construction.

Among the objects of the present invention are the following:

To provide new and useful oxygen cylinder carrier apparatus;

To provide new and useful oxygen cylinder carrier apparatus securable to an ambulance stretcher;

To provide new and useful oxygen cylinder carrier apparatus securable to the torso supportive frame of an ambulance stretcher;

To provide new and useful oxygen cylinder carrier apparatus having adjustable straps for securing the apparatus to a stretcher; and To provide a new and useful oxygen cylinder carrier apparatus including a bag for receiving the oxygen cylinder and straps for carrying the bag and cylinder and for securing the bag and cylinder to a stretcher.

Other and further advantages and features of this invention will become apparent to those skilled in the art from the ensuing description of a preferred embodiment of the invention, taken in conjunction with the accompanying drawings.

DESCRIPTION OF THE PREFERRED EMBODIMENT

Figure 1:
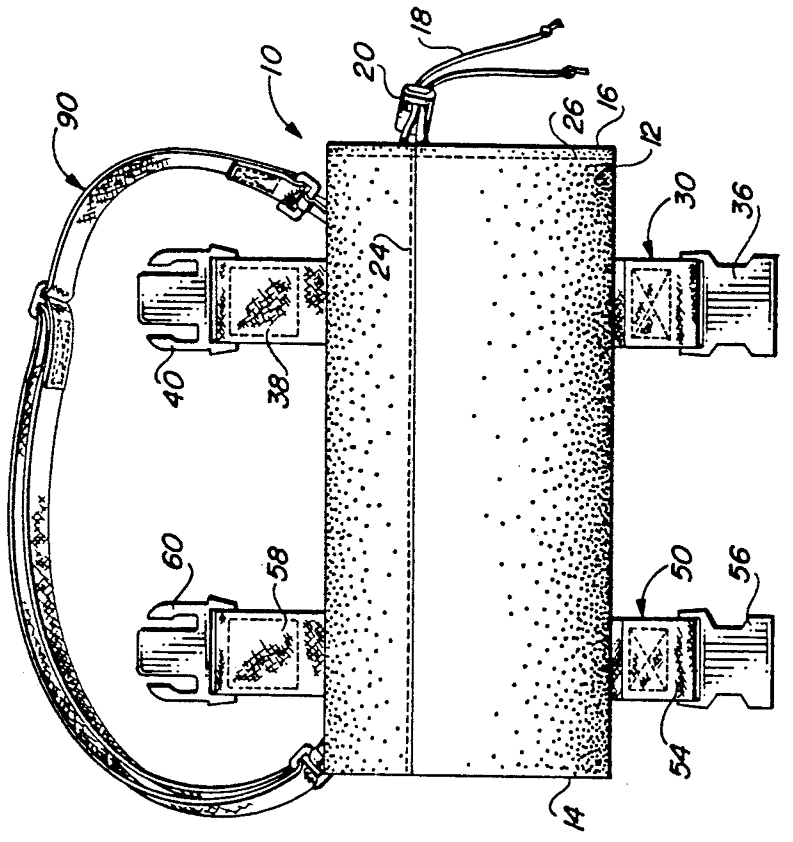
FIG. 1 is a top view from one side of the apparatus of the present invention as it appears prior to installation on a patient transport stretcher.

FIG. 1 shows a side view of oxygen bottle carrier apparatus 10 of the present invention.

Figure 2:
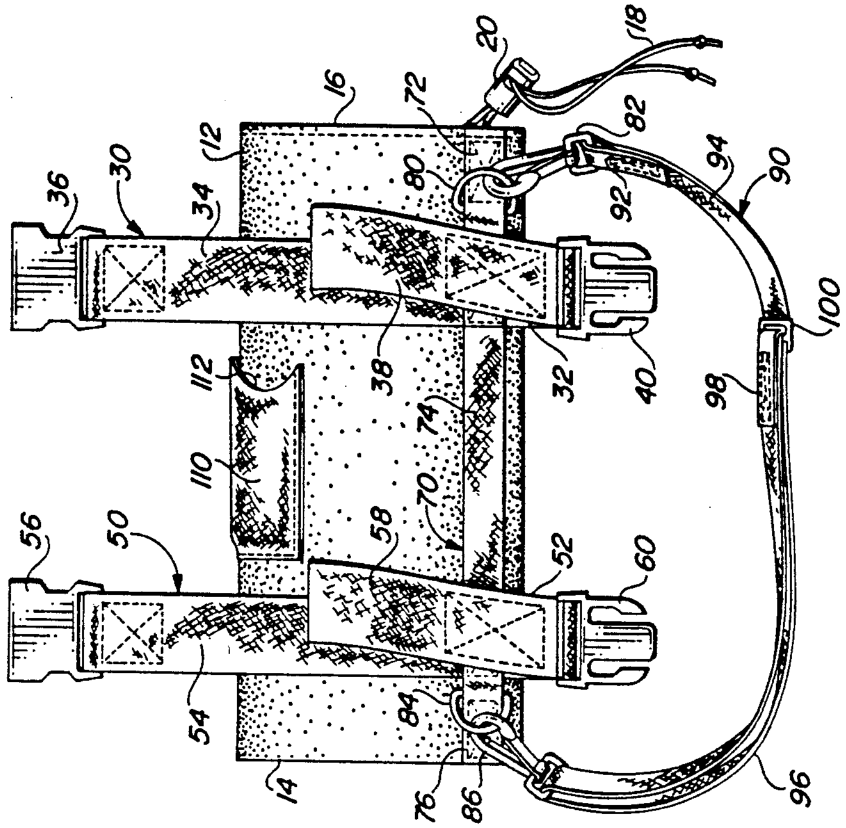
FIG. 2 is a top view of the apparatus of FIG. 1 rotated axially about one hundred eighty degrees showing the present invention prior to installation on the stretcher.
Figure 4:
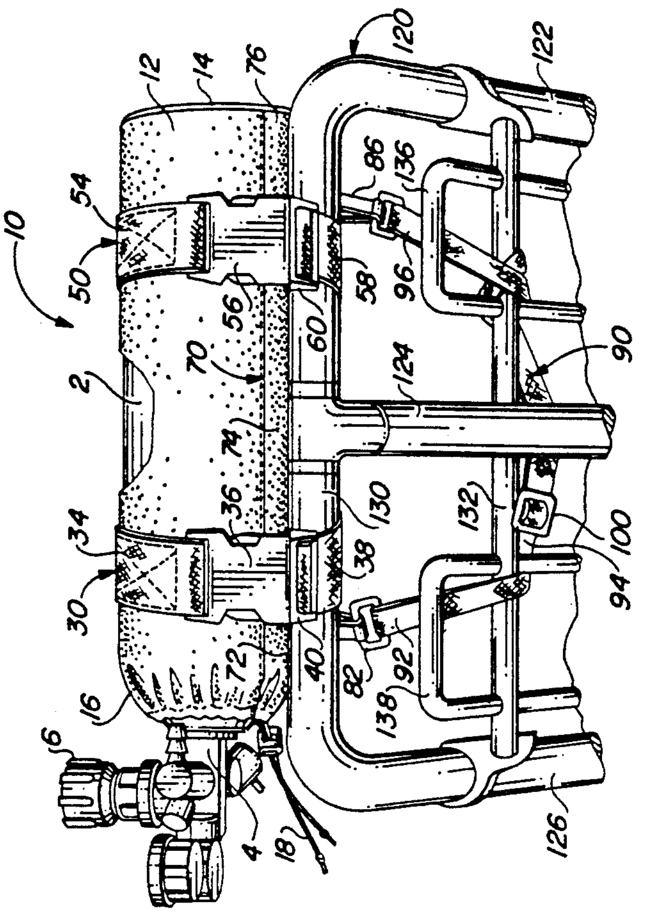
FIG. 4 is a bottom perspective view showing the apparatus of the present invention in its use environment.
Figure 3:
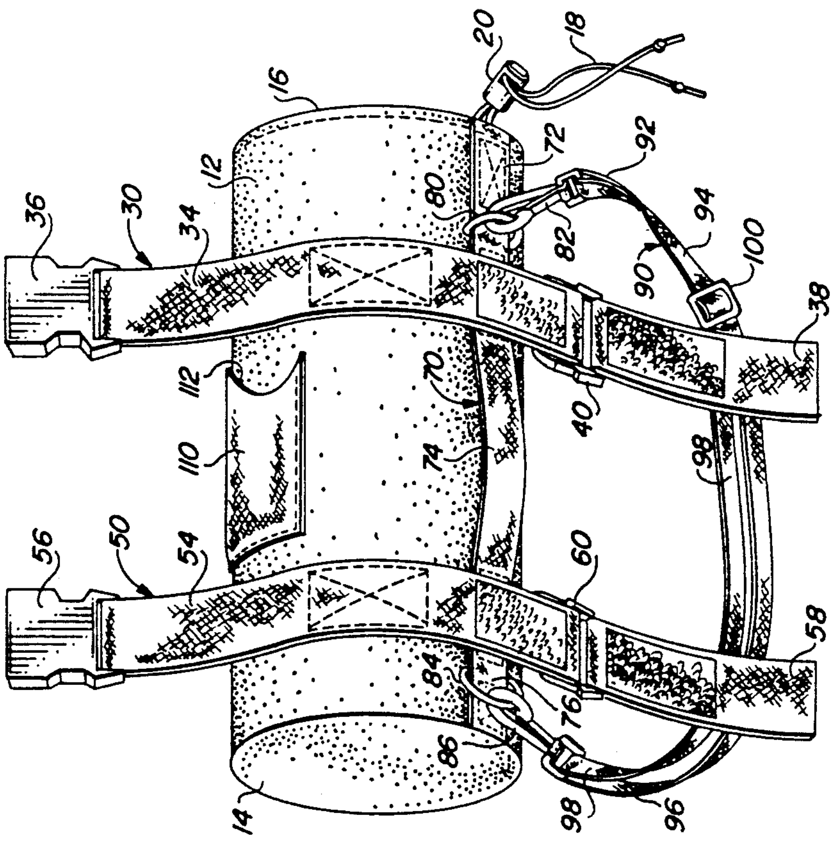
FIG. 3 is a perspective view of the apparatus of FIG. 2 ready for installation.

FIG. 2 comprises a side view of the apparatus 10 rotated about one hundred eighty degrees from that shown in FIG. 1. FIG. 3 comprises a perspective view of the apparatus 10 of FIG. 2, illustrating details of some of the elements of FIG. 2. FIG. 4 comprises a lower perspective view of the apparatus 10 in its use environment. For the following discussion, reference will generally be made to all four of the Figures.

The apparatus 10 includes a generally cylindrical bag 12, which may be a texturized, heavy duty, coated nylon fabric cloth bag, with attached straps and hardware. The bag 12 includes a closed end 14 and another end 16. The open end 16 allows for the insertion of a "D" size oxygen cylinder 2 (see FIG. 4) into the bag 12. Straps and hardware attached to the bag 12, allow for mounting the bag 12 to a patient transport stretcher 120 (see FIG. 4) of the kind commonly found on ambulances. The bag 12, which is sewn closed at the end 14, holds the "D" cylinder 2 inside, with only a stem portion 4 of the cylinder 2 and gauges and other accessories secured thereto, as shown in FIG. 4, protruding from the open end 16 of the bag.

Once the cylinder 2 is inserted into the bag 12 through the open end 16, the open end 16 is gathered closed using a drawstring 18 and it is held closed with a drawstring lock 20.

Secured to the bag 12 is a pair of straps 30 and 50. The strap 30 has an intermediate portion 32 appropriately secured to the bag 12. Extending outwardly from the intermediate portion 32 is another strap portion 34 with a female buckle portion 36 on its outer, free end. Extending outwardly from the intermediate portion 32, in the opposite direction from the outer portion 34, is a second outer strap portion 38. A male buckle portion 40 is secured to the outer, free end of the outer strap portion 38. The buckle 40 is adjustable on the strap portion 38.

The male portion 40 of the buckle is inserted into the female portion 36 of the buckle to form a closed loop with the strap 30 around both the bag 12 with the oxygen cylinder 2 therein, and the tubular framework of the patient transport stretcher 120 (see FIG. 4).

The strap 50 is substantially identical to the strap 30. The strap 50 includes an intermediate portion appropriately secured to the bag 12 and an outer end 54 to which is secured a female buckle portion 56. Outwardly from the intermediate portion 52 in a direction opposite to that of the end portion 54 is an end portion 58. A male buckle portion 60 is movably secured to the end portion 58.

The strap 50 is sewn to the bag 12 approximately three inches or so axially upwardly from the closed end 14 and a strap 30 sewn to the bag approximately three inches or so axially downwardly from the open but gathered closed end 16 of the bag 12.

Inside the closed loops of the straps 30 and 50 is the tubular framework of the patient transport stretcher 120, and utilizing these closed loops, the bag 10 is suspended from the tubular framework of the stretcher 120, supporting the weight of the "D" cylinder 2.

There is a pouch 110 formed of a small piece of strap or the like secured on three of its sides to the bag 12. There is a curved portion 112 which comprises an opening for the pouch. The pouch 110 is used to hold an "oxygen key" for turning the "D" cylinder 2 on and off.

There is a strap 70 extending longitudinally along the bag 12. The strap 70 includes three portions, a top portion 72 secured to the bag between the open end 16 and the strap 30, an intermediate portion 74 between the straps 30 and 50, and a bottom or lower portion 76 secured to the bag 12 between the strap 50 and the closed bottom 14. The intermediate portion 74 is not sewn to the bag, but may be used as a handle for handing or carrying the bag 12 and the oxygen bottle 2.

There is a strap 90 that is attached to the side of the bag 12 by a pair of snap hooks 82 and 86. The hooks 82 and 86 are approximately attached to the strap 90 at opposite ends. The snap hooks 82 and 86 are secured to "D" rings 84 and 86, respectively. The "D" rings 80 and 84 are appropriately secured to the strap portions 72 and 76, respectively.

The strap 90 includes an end portion 92 to which the snap hook 82 is secured. The strap 90 also includes an intermediate porion 94 extending from the end portion 92 to an end portion 98. There is a ladder buckle 100 secured to the end portion 98.

The strap hook 86 is secured to the intermediate strap portion 94, and a loop portion 96 of the strap is defined at the snap hook 86. The buckle 100 is movable on the intermediate strap portion 94, and accordingly the loop portion 96 moves along the strap portion 94 in response to the movement of the buckle 100.

The strap 90 allows for carrying the apparatus 10 on a shoulder, or allows for intertwining the strap 90 underneath the patient supporting surface, as shown in FIG. 4, and then tightening the strap 90 using the ladder lock buckle 100. Tightening the strap 90 allows for the apparatus 10 to be elevated slightly at the end of the patient transport stretcher 120, as shown in FIG. 4.

In both FIGS. 1 and 2, the straps 30 and 50 are shown open, ready to be connected to the stretcher structure 120. In FIG. 4, the straps 30 and 50, and also the strap 90, are shown connected to the stretcher 120.

In FIG. 3, the straps 30 and 50 are also shown unconnected, but ready to be wrapped about the framework of the stretcher 120. In FIG. 3, the ends 38 and 58 of the straps 30 and 50, respectively, are shown "open" or "out" as opposed to the partially "folded" orientation shown in FIG. 2. The buckles 40 and 60 may be moved or adjusted along the length of the strap portions 38 and 58, respectively. The strap portions 38 and 58 may then be folded along their lengths adjacent to the buckles and secured by hook and loop portions 42, 44 and 62, 64, respectively. In FIG. 4, the strap portions 38 and 58 are shown secured in their folded orientations.

In FIG. 4, a portion, the upper or head portion, of the stretcher 120 is shown as including longitudinal outside frame members 122 and 126, and an intermediate longitudinal frame member 124 between the frame members 122 and 126. The frame members 122 and 126 extend to an end cross member 130. The cross member 130 is a transversely extending frame member which comprises one end of the stretcher 120. The frame member 124 is appropriately secured to the frame member 130.

Extending between appropriately secured to the frame members 122 and 126 is a transverse frame member 132. The frame member 132 is parallel to, and spaced apart from, the end frame member 130. A pair of handle or grip elements 136 and 138 are secured to the frame member 132. The frame members are typically tubular, but the grip elements 136 and 138, and their extended elements, portions of which are shown in FIG. 4, are typically solid elements, substantially smaller in diameter than the tubular frame members.

The tubular frame member 130 is perpendicular to the two straps 30 and 50, with the straps 30 and 50 wrapped about the member 130. The apparatus 10 is suspended from the frame member 130. The bottle 2 is disposed in the bag 12 and the drawstring 18 and drawstring lock 20 are used to gather the open end 16 of the bag closed when the cylinder 2 is inserted into the bag. The shoulder/supporting strap 90 is intertwined or wound about the stretcher frame member 132 to allow for the apparatus 10 to be elevated slightly above the stretcher 120. Once the strap 90 is tightened using the slide lock buckle 100, the apparatus 10 is elevated approximately ninety degrees from the "6 o'clock" position to the "9 o'clock" position and is held in that position, as shown in FIG. 4.

FIG. 4 shows the apparatus 10 with a "D" cylinder 2 and an oxygen pressure regulator 6 mounted on the tubular framework of the stretcher 120. The view of FIG. 4 is generally from the bottom or underside, head-end of the stretcher 120. FIG. 4 shows merely one possible method of mounting the apparatus 10 to a stretcher. Other methods of mounting may become apparent to those personnel utilizing the apparatus.

We claim:

1. Oxygen cylinder carrier apparatus for securing an oxygen cylinder to a stretcher comprising, in combination:
   - bag means for receiving and holding an oxygen cylinder, including
     - a generally cylindrical bag;
     - an open end for receiving the oxygen cylinder, and a closed end;
   - first strap means secured to the bag means and extending generally circumferentially about the bag for securing the bag means to the stretcher; and
   - second strap means secured to the bag means adjacent to the open end and to the closed end and extending outwardly from the bag means for positioning the bag means in a desired orientation on the stretcher.

2. The apparatus of claim 1 in which the bag means further includes means for securing the open end of the bag about the oxygen cylinder.

3. The apparatus of claim 1 in which the bag means further includes third strap means secured to the bag and extending generally longitudinally along and in relation to the bag.

4. The apparatus of claim 3 in which the second strap means is generally secured to the third strap means.

5. The apparatus of claim 3 in which the third strap means includes a handle portion for carrying the bag.

6. The apparatus of claim 1 in which the first strap means comprises a pair of straps spaced apart from each other and each strap of the pair extends generally circumferentially relative to the bag.

7. The apparatus of claim 6 in which the second strap means includes
   - a first end portion secured to the bag,
   - a second end portion,
   - an intermediate portion between the first and second end portions,
   - a buckle secured to the second end portion and movable on the intermediate portion to define a loop portion on the intermediate portion remote from the first end portion, and
   - means for securing the loop portion to the bag remote from the first end.

8. The apparatus of claim 1 in which the bag means further includes a pouch secured to the bag for holding a tool for the oxygen cylinder.

* * * * *